United States Patent

Naeff et al.

[11] Patent Number: 5,834,016
[45] Date of Patent: Nov. 10, 1998

[54] LIPOSOME-BASED TOPICAL VITAMIN D FORMULATION

[75] Inventors: Rainer Naeff, Langwiesen; Sandro Delmenico; Rene Spycher, both of Schaffhausen, all of Switzerland; Mike Corbo, Flemington, N.J.; Frank Flother, Schaffhausen, Switzerland

[73] Assignee: Cilag AG, Switzerland

[21] Appl. No.: 814,049

[22] Filed: Mar. 6, 1997

Related U.S. Application Data

[60] Provisional application No. 60/014,805, Apr. 9, 1996.

[51] Int. Cl.$^6$ .................................................. A61K 9/127
[52] U.S. Cl. ............................................................ 424/450
[58] Field of Search ............................................ 424/450

[56] References Cited

U.S. PATENT DOCUMENTS

| Re. 33,107 | 11/1989 | Dikstein et al. | |
|---|---|---|---|
| 4,708,861 | 11/1987 | Popescu | 424/1.1 |
| 5,597,575 | 1/1997 | Breitbarth | 424/401 |
| 5,616,602 | 4/1997 | Tayler | 514/410 |
| 5,631,394 | 5/1997 | Wei | 556/404 |

FOREIGN PATENT DOCUMENTS

| 0 253 619 | 7/1987 | European Pat. Off. . |
| WO 95/35095 | 12/1995 | European Pat. Off. . |
| WO 96/37193 | 11/1996 | European Pat. Off. . |
| 2 660 192 | 10/1991 | France . |

OTHER PUBLICATIONS

International Search Report International Application No PCT/US97/04778 Dated Aug. 14, 1997.

Journal of Drug Targeting, vol. 2, No. 5, 1994, US, pp. 419–429, XP002037785, K. Prufer et al. Interaction of Liposomal Incorporated Vitamin D3–Analogues and Human Keratinocytes.

*Primary Examiner*—Gollamudi S. Kishore
*Attorney, Agent, or Firm*—Kenneth J. Dow

[57] ABSTRACT

A liposome-based formulation with good skin penetration of the effective substance, particularly calcitriol, is described. This formulation is well suited for the treatment of psoriasis.

7 Claims, 2 Drawing Sheets

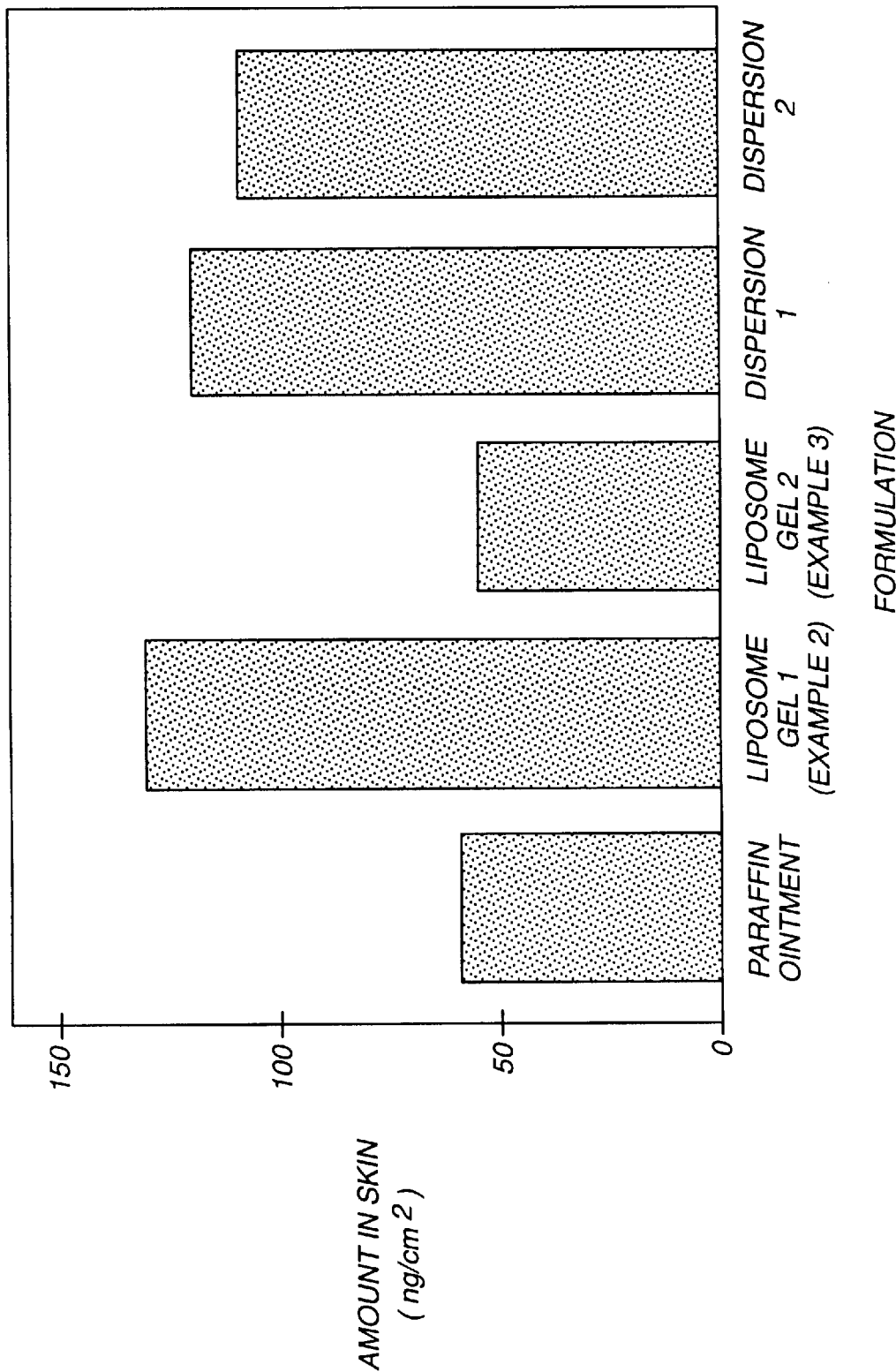

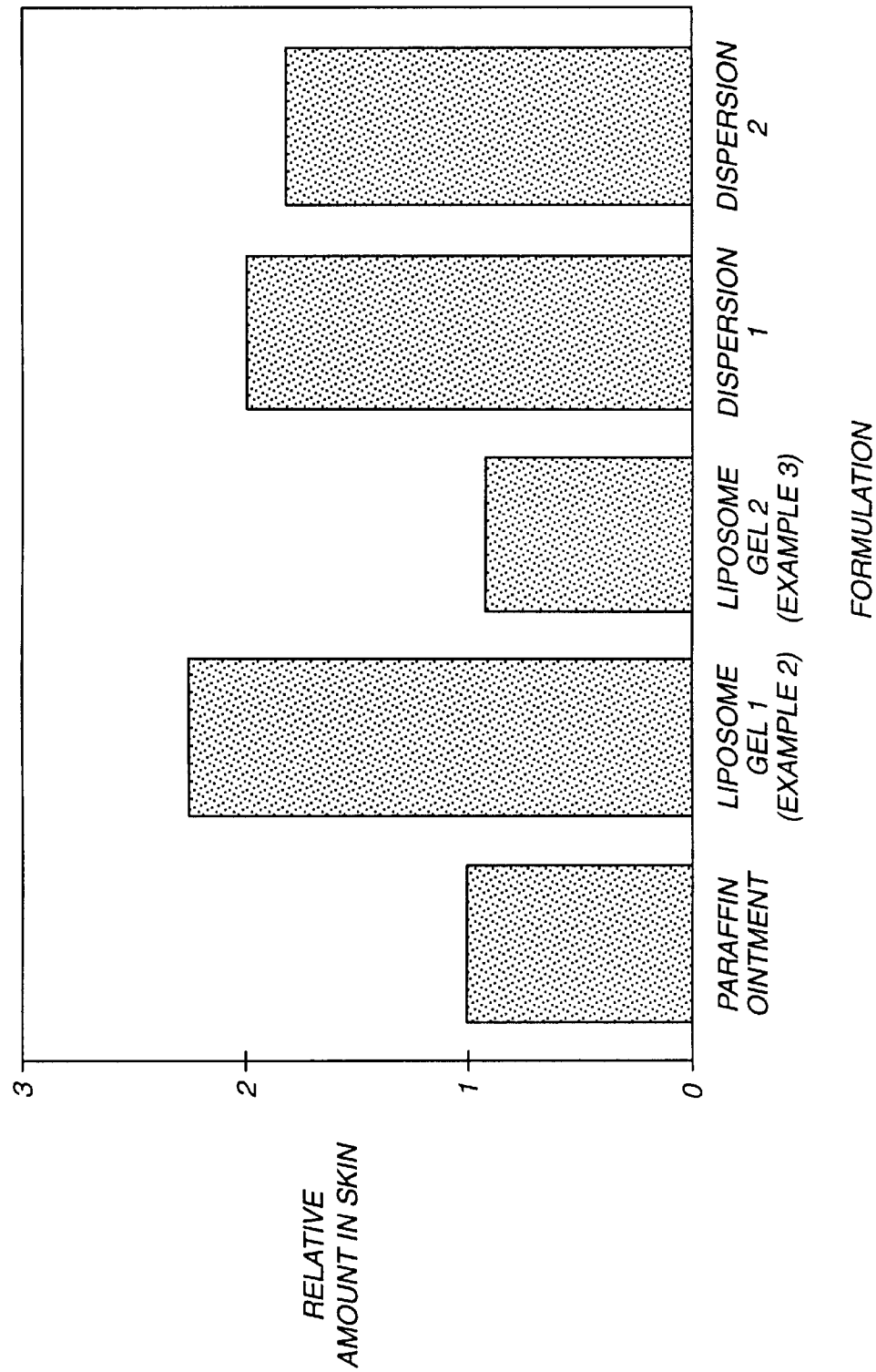

5,834,016

LIPOSOME-BASED TOPICAL VITAMIN D FORMULATION

This application is a continuation of the provisional application No. 60/014,805 filed Apr. 9, 1996.

FIELD OF THE INVENTION

The present invention relates to a liposome based topical formulation, particularly a formulation providing good penetration of biological active substances into the skin, and being particularly suitable for the treatment of psoriasis. In particular, the invention relates to a liposome based formulation for the topical treatment of psoriasis containing Vitamin D, or a derivative thereof, particularly calcitriol, as an active ingredient.

BACKGROUND OF THE INVENTION

In recent years there has been much interest in topical treatment of psoriasis and other skin disorders with vitamin D and derivatives thereof. For example, U.S. Pat. No. RE 33,107 discloses compositions containing 1α,25-dihydroxycholecalciferol (calcitriol) and related compounds as active ingredient for the topical treatment of skin disorders including psoriasis. Such treatment nowadays is preferably performed using a paraffin ointment base. The penetration of the effective substance into the skin from such a paraffin ointment base is rather low, however.

Due to the fact that paraffin ointments are very greasy, patient compliance is only moderate. Up to 80% of psoriasis lesions are occurring in hairy regions. Therefore, patients generally prefer a topical formulation that can be washed off.

Liposomes are small vesicles comprising amphipathic lipids arranged in spherical bilayers. Liposomes may contain many concentric lipid bilayers separated by aqueous channels (multilamellar vesicles or MLVs), or alternatively, they may contain a single membrane bilayer (unilamellar vesicles), which may be small unilamellar vesicles (SUVs) or large unilamellar vesicles (LUVs). The lipid bilayer is composed of two lipid monolayers having a hydrophobic "tail" region and a hydrophilic "head" region. In the membrane bilayer, the hydrophobic "tails" of the lipid monolayers orient towards the center of the bilayer, whereas the hydrophilic "heads" orient toward the aqueous phase.

Liposomes may be used to encapsulate a variety of materials by trapping hydrophilic compounds in the aqueous interior or between bilayers, or by trapping hydrophobic compounds within the bilayer. As such, they are particularly useful to deliver biologically active materials by encapsulating compounds which exhibit poor aqueous solubility or which exhibit unacceptable toxicity at therapeutic dosages. Topical liposome formulations are already known for years. For example WO 85/03640 describes formulations in which the liposomes are sequestered in a gel matrix whereby the type of the gel is described as having no influence on the liberation rate of effective substances with a molecular weight of less than about 2000 Daltons.

A specific method for the production of liposomes with only one double layer is disclosed in EP 253 619.

The goal of the present invention therefore was to provide a topical application form suitable for vitamin D and its derivatives, particularly calcitriol, which is less greasy than the usual paraffin ointments and at the same time provides good skin penetration abilities. Independently therefrom, the formulation should also provide a good skin hydration.

SUMMARY OF THE INVENTION

A liposome-based composition for use in the topical treatment of skin disorders comprising:

(a) an effective amount of vitamin D or a derivative thereof;

(b) lecithin or hydrogenated lecithin;

(c) cholesterol or a derivative thereof selected from cholesterol esters, polyethylene glycol derivatives of cholesterol (PEG-cholesterols), and organic acid derivatives of cholesterols; and (d) a lower alcohol(preferably ethanol).

Preferably, the Vitamin D compound as active ingredient is 1α,25-dihydroxycholecalciferol (calcitriol) or 1α-hydroxycholecalciferol.

BRIEF DESCRIPTION OF THE DRAWINGS

FIG. 1—shows the amount of calcitriol in the skin following application of the composition of the invention, and FIG. 2—shows the relative amount of calcitriol in the skin, compared to a paraffin ointment base.

DETAILED DESCRIPTION

The active ingredients used in the present invention are the Vitamin D compounds in general, and particularly the compounds 1α,25-dihydroxycholecalciferol (calcitriol) or 1α-hydroxycholecalciferol or mixtures thereof. The compositions are useful in treating dermatological disorders including psoriasis, eczema, dermatitis, dry skin, solar keratosis, and the like.

The liposome compositions generally contain from about 300 μg to about 5000 μg of the Vitamin D compound per 100 grams of composition. Such a formulation, particularly produced according to the process described in EP 0 253 619, which is herein incorporated by reference, shows very good penetration abilities of vitamin D and its derivatives and related compounds, particularly calcitriol, when applied in psoriasis treatment.

Lecithin can either be used as natural lecithin in purified form or, preferably, as the more stable hydrogenated lecithin, whereby the use of the latter allows a reduction of the concentration of the stabilizing agents. The lecithin component is generally present in an amount from about 1.0 to 10 grams per 100 grams of composition.

Cholesterol is employed as the liposome stabilizing agent in amounts ranging from 0.1 to 1.0 grams per 100 grams of composition. In addition to cholesterol, other cholesterol derivatives may be employed such as cholesterol esters, polyethylene glycol derivatives of cholesterol (PEG-cholesterols), as well as organic acid derivatives of cholesterols, for example cholesterol hemisuccinate.

The alcohol component is a lower alkanol of one to six carbon atoms, such as methanol, ethanol, n-propanol, isopropanol, n-butanol and the like in amounts ranging from 0.5 to about 8.0 grams per 100 grams of composition. Ethanol is preferred.

Dependent on the amount to be applied and/or the place of application, the use of highly fluid products for topical application of Vitamin D is unfavorable. It is therefore advantageous to include a gelling agent in the composition to provide a less fluid product. As already mentioned above, it is already known from WO 85/03640 to sequester liposomes in a gel matrix whereby, according to said state of the art document, the gelling agent shall have no influence on the liberation rate of an effective substance with a molecular weight of less than about 2000 Daltons. Surprisingly, however, it has now been found that contrary to the teachings of WO 85/03640, the type of gelling agent can have great influence on the liberation rate of the effective substance. It has been found that a liposomal formulation as described above, but additionally comprising one or more a polyacrylate(s) such as carboxypolymethylene (carbomer) as gelling agent, makes possible a much better skin penetration of the active ingredient e.g. Calcitriol than do e.g. paraffin ointment bases or liposome-based formulations with e.g. xanthan gum as gelling agent. By the use of polyacrylate (s) as gelling agent(s), the penetration abilities of the highly fluid liposome-based formulations are at least reached or even enhanced.

Using hydrogenated lecithin as the lecithin, at a pH of about 7.4, which is appropriate for calcitriol as the effective substance and polyacrylate as the gelling agent, stable topical formulations are obtained, i.e. the liposomes themselves are stable and at the same time the decomposition of the biologically effective substance is minimized.

By the improved penetration characteristics of the inventive formulations the number of the administrations per day can be diminished because of the greater amount of biologically effective compound in the skin and therewith also the amount of pharmaceutical preparation, which is or has to be applied.

The stability of the composition can be further enhanced by the addition of antioxidants such as tocopherol, butylated hydroxytoluene, butylated hydroxyanisole, ascorbyl palmitate, or edetates such as e.g. disodium edetate, with the edetates additionally binding possibly present heavy metals. The stability can furthermore be enhanced by the addition of preserving agents such as benzoic acid and parabens, e.g. methylparaben, and/or propylparabene. The desired pH is preferably stabilized by a buffer system. For Calcitriol as the effective substance a phosphate buffer, particularly a buffer of potassium dihydrogen phosphate and disodium hydrogen phosphate, or a citric acid buffer are suitable.

The protons that are liberated upon thickening or cross-linkage, respectively, of the polyacrylate (e.g. Carbomer 974 P), are neutralized by the addition of a base, preferably sodium hydroxide.

One or more additional substances which have therapeutic affects on the skin may also be incorporated into the liposome compositions of the present invention. Such additional substances which may be incorporated include compounds capable of inducing epitheliazation, such as the retinoids, or the chromanols such as Vitamin E. Anti-inflammatory agents such as corticosteroids may also be advantageously included in the composition. Such corticosteroids include, for example, hydrocortisone or its acetate in amounts ranging from 0.25–5% by weight of the composition. Keratoplastic agents such as anthralin and coal tar may also be included in the composition.

The liposome-based compositions of the present invention, particularly the ones that are thickened by polyacrylates are of course, also suitable for many other pharmaceutical applications in addition to psoriasis. As disclosed in U.S. Pat. No. RE 33,107, hereby incorporated by reference, the compositions of the invention may be applied therapeutically in the treatment of dermatitits (contact and atopic), eczema, solar keratosis and wound healing. The compositions may also be used in cosmetic applications for the topical treatment of wrinkles, dry skin, and skin slackness.

Very good penetration, particularly for Calcitriol as the effective substance, has been found for the following composition:

|  | $\mu$g/100 g |
| --- | --- |
| Calcitriol or analogous compounds | 315–5000 |

|  | g/100 g |
| --- | --- |
| Lecithin | 1.0–10.000 |
| Cholesterol | 0.1–1.000 |
| Ethanol | 0.5–8.000 |
| Tocopherol | 0.0–0.100 |
| Methylparaben | 0.0–0.150 |
| Propylparaben | 0.010–0.05 |
| Potassium dihydrogen phosphate | 0.0–0.05 |
| di-Sodium hydrogen phosphate dihydrate | 0.0–0.15 |
| Disodium edetate | 0.001–0.1 |
| Sodium hydroxide | 0.0–0.9 |
| Carbomer 974 P | 0.0–1.6 |
| Water purified | ad 100.0 |

The liposome-based compositions of the present invention may be prepared by applying the methods known in the art for manufacturing liposome compositions. Liposomes and related phospholipid vesicle complexes can be prepared by a variety of techniques. In general, these techniques start with "dry" lipids that are introduced into an aqueous phase (D. Lasic, J.Theor. Biol. (1087) 124:35–41). Once the lipid is hydrated, liposomes form spontaneously. Techniques have been developed to control the number of lamellae in the liposome and to produce defined particle size. One commonly used method, as described by Bangham et al. (J. Mol. Biol. 13:238–252 (1965), starts by dissolving the lipid and lipophilic substance in an organic solvent. The solvent is then removed under reduced pressure by rotary evaporation and the lipid forms a thin film on the wall of the container. Upon the addition of an aqueous solution, large multilamellar liposomes are formed when the mixture is agitated. Small unilamellar vesicles can be prepared by sonication of the large multilamellar vesicles.

A preferred method for use in the present invention is described in EP 253619, hereby incorporated by reference. In this method single bilayered liposomes are prepared by preparing an ethanolic solution of a phospholipid and the active ingredient and injecting the solution under pressure into an aqueous electrolyte solution contained in a high speed homogenizer. The liposomes are formed spontaneously.

The particular advantages of the present invention are further illustrated by the following examples:

EXAMPLE 1

Liposome-Based Dispersion

A liposome-based dispersion of the following composition was produced according to the method described in EP 0 253 619:
Composition:

|  | $\mu$g/100 g |
| --- | --- |
| Calcitriol | 315 |

|  | g/100 g |
| --- | --- |
| Lecithin (Soya) hydrogenated | 5.000 |
| Cholesterol | 1.000 |
| Ethanol | 8.000 |
| Tocopherol | 0.010 |

-continued

|  |  |
|---|---|
| Methylparaben | 0.140 |
| Propylparaben | 0.010 |
| Potassium dihydrogen phosphate | 0.026 |
| di-Sodium hydrogen phosphate dihydrate | 0.144 |
| Disodium edetate | 0.010 |
| Water purified | 85.660 |

Procedure:

Methylparaben and propylparaben and the disodium edetate were dissolved in purified water at 80° C. (kettle I). Calcitriol, tocopherol, lecithin, and cholesterol were dissolved in ethanol in a separate kettle (kettle II) at 55° C.–70° C. under agitation. The ethanol solution was purged with nitrogen during the whole procedure. The water phase was cooled to 55° C.–70° C. Kettle 1 was connected to a high-performance homogenizer (Megatron MT-48; manufacturer: Kinematica, Littau, Lucerne, Switzerland) to effect circulation of the aqueous solution.

The ethanol solution was injected through a tube from kettle II directly into the homogenizer. Liposomes having a diameter of less than 2.5 μm were spontaneously formed and collected in kettle I.

Technical Data:

Homogenizer speed: up to 13,000 rpm

Flow rate of the ethanol solution: 20–100 ml/s

EXAMPLE 2

Liposome-Based Gel

Composition:

|  | μg/100 g |
|---|---|
| Calcitriol | 315 |

|  | g/100 g |
|---|---|
| Lecithin (Soya) hydrogenated | 5.000 |
| Cholesterol | 1.000 |
| Ethanol | 8.000 |
| Tocopherol | 0.010 |
| Methylparaben | 0.140 |
| Propylparaben | 0.010 |
| Potassium dihydrogen phosphate | 0.026 |
| di-Sodium hydrogen phosphate dihydrate | 0.144 |
| Disodium edetate | 0.010 |
| Sodium hydroxide | 0.396 |
| Carbomer 974 P | 0.800 |
| Water purified | 84.464 |

Procedure:

The production of the liposome-based gel was performed as the one of the dispersion according to Example 1 with the exception that after the liposome formation according to Example 1 the Carbomer 974 P was admixed, followed by a sodium hydroxide solution.

Technical Data:

Homogenizer speed: up to 13,000 rpm

Flow rate of the ethanol solution: 20–100 ml/s

EXAMPLE 3

Liposome-Based Gel with Xanthan Gum

Composition:

|  | μg/100 g |
|---|---|
| Calcitriol | 315 |

|  | g/100 g |
|---|---|
| Lecithin (Soya) hydrogenated | 5.000 |
| Cholesterol | 1.000 |
| Ethanol | 8.000 |
| Tocopherol | 0.010 |
| Methylparaben | 0.140 |
| Propylparaben | 0.010 |
| Potassium dihydrogen phosphate | 0.026 |
| di-Sodium hydrogen phosphate dehydrate | 0.144 |
| Disodium edetate | 0.010 |
| Xanthan Gum | 2.200 |
| Water purified | 83.460 |

Procedure:

The production was performed as described in Example 2, except that instead of the Carbomer 974 P, xanthan gum was added. Because of the amended gelling agent the sodium hydroxide addition became unnecessary.

Technical Data:

Identical to those of Example 2.

EXAMPLE 4

Comparative Tests on Skin Penetration

The skin penetration of Calcitriol from the products produced as described in Examples 1 to 3 and a commercially available product was determined in vitro, whereby two independently produced products according to Example 1 were used.

The penetration study was performed under the following conditions:

Diffusion Cells: Modified Franz Cell, 13 ml volume, 3.14 $CM^2$ surface area

Skin: Human, leg, split-thickness

Receptor Media: Water

Temperature: 32° C.

Study Duration: 24 hours

Amount of Formulation Applied: Approximately 1 ml

Conditions: Skin surface not occluded; study conducted under yellow lights & darkness.

Skin samples were mounted onto Franz Diffusion Cells, and approximately 1 ml of each formulation was applied and spread evenly on the skin surface. Skin surfaces with formulations were exposed to room air (RH approximately 40%) throughout the study period. After 24 hours, the skin samples were observed, removed from the diffusion cells, and excess formulation was removed using a "Kim-Wipe". The skin surface was then cleaned with ethanol-soaked "Kim-Wipes" (3×) to remove any residual formulation/drug.

Skin samples were extracted with 2 ml ethanol to recover calcitriol which had penetrated into the skin. Following extraction, the ethanol solution was assayed for calcitriol by HPLC with UV detection. The amount of calcitriol extracted from the skin sample gave the following results:

Results and Discussion

Upon completion of the 24 hour study, the commercial paraffin-based ointment formulation remained unchanged on the skin surface. However, as expected, all of the liposome formulations had dried, leaving a thin-film residue on the skin surface.

The results from the in vitro skin penetration study indicate that the liposome gel manufactured with Carbomer 974 P achieved calcitriol skin levels approximately 2-fold higher than the paraffin-based ointment or the liposome gel formulation with xanthan gum as the gelling agent, respectively.

The dispersion formulations according to Example 1 behaved similar to the Carbomer gel formulation, in producing calcitriol skin levels approximately 2-fold higher than the paraffin-based ointment.

The amounts of calcitriol in the skin are shown in FIG. 1, the relative amounts in FIG. 2.

We claim:

1. A liposome-based formulation comprising:
   (a) a dermatologically effective amount of vitamin D or a derivative thereof selected from the compounds 1α,25-dihydroxycholecalciferol and 1α-hydroxycholecalciferol or mixtures thereof;
   (b) lecithin or hydrogenated lecithin;
   (c) cholesterol or a derivative thereof selected from cholesterol esters, polyethylene glycol derivatives of cholesterol (PEG-cholesterols), and organic acid derivatives of cholesterols;
   (d) an alcohol of one to six carbon atoms.

2. The liposome-based formulation of claim 1, wherein the lower alcohol is ethanol.

3. The liposome-based formulation of claim 1, wherein the vitamin D or a derivative therefrom is Calcitriol.

4. The liposome-based formulation of claim 1, wherein the lecithin is hydrogenated lecithin.

5. The liposome-based formulation of claim 1, characterized in that it furthermore comprises preserving agents, antioxidants or complexing agents.

6. The liposome-based formulation of claim 2, characterized in that it has the following composition:

| | μg/100 g |
|---|---|
| Vitamin D or a derivative thereof selected | 315–5000 |
| from the compounds 1α,25-dihydroxycholecalciferol and 1α-hydroxycholecalciferol or mixtures thereof | g/100 g |
| Lecithin | 1.0–10.000 |
| Cholesterol | 0.1–1.000 |
| Ethanol | 0.5–8.000 |
| Tocopherol | 0.0–0.100 |
| Methylparaben | 0.0–0.150 |
| Propylparaben | 0.010–0.05 |
| Potassium dihydrogen phosphate | 0.0–0.05 |
| di-Sodium hydrogen phosphate dihydrate | 0.0–0.15 |
| Disodium edetate | 0.001–0.1 |
| Sodium hydroxide | 0.0–0.9 |
| Carbomer 974 P | 0.0–1.6 |
| Water purified | ad 100.0 |

7. The liposome-based formulation of claim 1 for use as a pharmaceutical preparation for the treatment of psoriasis.

* * * * *